United States Patent
Worm et al.

(10) Patent No.: US 10,711,119 B2
(45) Date of Patent: Jul. 14, 2020

(54) CARRAGEENAN-BASED COMPOSITIONS FOR FILMS AND CAPSULES

(71) Applicant: CP Kelco ApS, Lille Skensved (DK)

(72) Inventors: Thomas Worm, Køge (DK); Jens Eskil Trudsø, Roskilde (DK)

(73) Assignee: CP Kelco ApS, Lille Skensved (DK)

( * ) Notice: Subject to any disclaimer, the term of this patent is extended or adjusted under 35 U.S.C. 154(b) by 2 days.

(21) Appl. No.: 16/170,120

(22) Filed: Oct. 25, 2018

(65) Prior Publication Data

US 2019/0211189 A1 Jul. 11, 2019

Related U.S. Application Data

(60) Provisional application No. 62/615,460, filed on Jan. 10, 2018.

(51) Int. Cl.
| | | |
|---|---|---|
| *C08L 5/00* | (2006.01) | |
| *C08J 5/18* | (2006.01) | |
| *A61K 9/48* | (2006.01) | |
| *C08L 3/00* | (2006.01) | |
| *A61K 47/36* | (2006.01) | |
| *C08K 5/053* | (2006.01) | |
| *C08L 3/02* | (2006.01) | |

(52) U.S. Cl.
CPC .............. *C08L 5/00* (2013.01); *A61K 9/4816* (2013.01); *A61K 47/36* (2013.01); *C08J 5/18* (2013.01); *C08L 3/00* (2013.01); *C08J 2305/00* (2013.01); *C08J 2403/02* (2013.01); *C08K 5/053* (2013.01); *C08L 3/02* (2013.01)

(58) Field of Classification Search
CPC ........... C08L 5/00; C08L 3/00; A61K 9/4816; A61K 47/36; C08J 5/18; C08J 2305/00; C08J 2403/02; C08K 5/053
See application file for complete search history.

(56) References Cited

U.S. PATENT DOCUMENTS

| | | |
|---|---|---|
| 6,340,473 B1 | 1/2002 | Tanner et al. |
| 6,582,727 B2 | 6/2003 | Tanner et al. |
| RE39,079 E | 4/2006 | Tanner et al. |
| 7,816,341 B2 | 10/2010 | Sewall et al. |
| 8,231,896 B2 | 7/2012 | Tanner et al. |
| 8,293,285 B2 | 10/2012 | Trudsoe |
| 8,404,289 B2 | 3/2013 | Trudsoe |
| 2005/0013847 A1* | 1/2005 | Ballard ............... A61K 8/0208 424/439 |
| 2005/0014852 A1 | 1/2005 | Sewall et al. |
| 2005/0106233 A1* | 5/2005 | Andersen ............ A61K 9/4883 424/451 |
| 2008/0317789 A1 | 12/2008 | Trudso |

FOREIGN PATENT DOCUMENTS

| | | |
|---|---|---|
| CN | 101229450 | 7/2008 |
| EP | 1 115 748 | 2/2000 |
| EP | 1 598 062 | 11/2005 |
| WO | WO 98/42294 | 10/1998 |
| WO | WO 00/06609 | 2/2000 |

OTHER PUBLICATIONS

Alphons C. J. Voragen et al., "Polysaccharides," in 29 Ullmann's Encyclopedia of Industrial Chemistry 417, published online 2003.*
International Search Report and the Written Opinion of the International Searching Authority in PCT/EP2018/084233 dated Jun. 7, 2019, 12 pages.

* cited by examiner

*Primary Examiner* — Nicholas E Hill
(74) *Attorney, Agent, or Firm* — Merchant & Gould P.C.

(57) ABSTRACT

Carrageenan-based compositions containing a carrageenan, a starch, a plasticizer, water, and an optional buffer are disclosed, in which the carrageenan has both a potassium content of less than 4 wt. % and a viscosity configured to produce capsules on pressure-free rotary die equipment. Films and capsules can be formed from the carrageenan-based compositions.

26 Claims, No Drawings

CARRAGEENAN-BASED COMPOSITIONS FOR FILMS AND CAPSULES

REFERENCE TO RELATED APPLICATION

This application claims the benefit of U.S. Provisional Application Ser. No. 62/615,460, filed on Jan. 10, 2018, the disclosure of which is incorporated herein by reference in its entirety.

FIELD OF THE INVENTION

The present invention relates to compositions containing a carrageenan, a starch, a plasticizer, and water, and to films, capsules, and other articles of manufacture prepared from the carrageenan-based compositions.

BACKGROUND OF THE INVENTION

Soft gelatin capsules are commonly used to encapsulate solid and liquid materials, such as nutritional or pharmaceutical products, for oral administration. Typical methods and equipment for gelatin encapsulation are described in WO 98/42294. The use of gelatin to form capsules, however, has drawbacks that include the high cost, often inadequate supply, and tendency to cross-link.

Thus, compositions are needed that mimic the behavior and characteristics of mammalian gelatin, and that can be used to efficiently produce soft capsules, while overcoming the shortcomings of gelatin. Accordingly, it is to these ends that the present invention is principally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Compositions comprising a carrageenan, a starch, a plasticizer, water, and an optional buffer are disclosed and described herein. The carrageenan can have a potassium content of less than or equal to about 4 wt. % and can be characterized by a viscosity of from about 10 to about 55 cP. The carrageenan also can have a potassium content in a range from about 0.5 to about 2 wt. % and can be characterized by a viscosity of from about 25 to about 45 cP. This viscosity is the viscosity of a 0.1 M aqueous sodium chloride solution containing 1.5 wt. % of the carrageenan at 75° C. Additionally, the carrageenan can be further characterized by a viscosity of an aqueous solution containing 1.5 wt. % of the carrageenan at 75° C. (without sodium chloride) that typically falls within a range from about 30 to about 80 cP, or from about 35 to about 80 cP.

Generally, the carrageenan can comprise an iota carrageenan, and the composition can contain from about 2.5 to about 10 wt. % carrageenan, or from about 4 to about 9 wt. % carrageenan (or from about 8 to about 17 wt. % carrageenan on a dry basis). In the composition, starch often is present in an amount greater than that of the carrageenan; for instance, the weight ratio of starch:carrageenan can range from about 1.5:1 to about 5:1.

Also disclosed herein are articles of manufacture containing the carrageenan compositions, such as films or capsules.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and each and every feature disclosed herein, all combinations that do not detrimentally affect the designs, compositions, processes, or methods described herein are contemplated and can be interchanged, with or without explicit description of the particular combination. Accordingly, unless explicitly recited otherwise, any aspect or feature disclosed herein can be combined to describe inventive designs, compositions, processes, or methods consistent with the present disclosure.

While compositions and methods are described herein in terms of "comprising" various components or steps, the compositions and methods also can "consist essentially of" or "consist of" the various components or steps, unless stated otherwise.

The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, and so forth.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. As a representative example, the viscosity of the carrageenan can be in certain ranges in various aspects of this invention. By a disclosure that the viscosity of the carrageenan (measured in a 0.1 M aqueous sodium chloride solution containing 1.5 wt. % of the carrageenan at 75° C.) is in a range from about 10 to about 55 cP, the intent is to recite that the viscosity can be any viscosity within the range and, for example, can be equal to about 10, about 15, about 20, about 25, about 30, about 35, about 40, about 45, about 50, or about 55 cP. Additionally, the viscosity can be within any range from about 10 to about 55 cP (for example, from about 25 to about 45 cP), and this also includes any combination of ranges between about 10 and about 55 cP (for example, the viscosity can be in a range from about 10 to about 20 cP or from about 25 to about 40 cP). Further, in all instances, where "about" a particular value is disclosed, then that value itself is disclosed. Thus, the disclosure of a viscosity range from about 10 to about 55 cP also discloses a viscosity range from 10 to 55 cP (for example, from 25 to 45 cP), and this also includes any combination of ranges between 10 and 55 cP (for example, the viscosity can be in a range from 10 to 20 cP or from 25 to 40 cP). Likewise, all other ranges disclosed herein should be interpreted in a manner similar to this example.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

DETAILED DESCRIPTION OF THE INVENTION

Disclosed herein are compositions containing a carrageenan, a starch, a plasticizer, water, and an optional buffer. The carrageenan can have a potassium content of less than or equal to about 4 wt. % (or from about 0.5 to about 3 wt. %), and can be characterized by a viscosity of from about 10 to about 55 cP, or from about 25 to about 45 cP (as measured in a 0.1 M aqueous sodium chloride solution containing 1.5 wt. % of the carrageenan at 75° C.), and/or characterized by a viscosity of from about 30 to about 80 cP, or from about 35 to about 80 cP (as measured in an aqueous solution containing 1.5 wt. % the carrageenan at 75° C.). Often, the composition can comprise an iota carrageenan in an amount ranging from about 2.5 to about 10 wt. % carrageenan, or from about 4 to about 9 wt. % carrageenan, based on the total weight of the composition (or from about 8 to about 17 wt. % carrageenan on a dry basis).

Beneficially, these compositions can be converted into films or capsules, and can be used as "drop in" replacements for traditional gelatin-based capsule formulations, without having to change the capsule forming equipment or operating parameters. Thus, beneficially, the disclosed compositions and films can be processed on standard pressure-free rotary die equipment to produce soft capsules.

Carrageenan-Based Compositions

The compositions disclosed and described herein can comprise a carrageenan, a starch, a plasticizer, and water. Such carrageenan-based compositions can be configured to produce capsules on pressure-free rotary die equipment. The carrageenan can have a relatively low potassium content (e.g., less than or equal to about 4 wt. %), and can be characterized by a viscosity configured to produce capsules on pressure-free rotary die equipment (e.g., a viscosity from about 10 to about 55 cP for a 0.1 M aqueous sodium chloride solution containing 1.5 wt. % of the carrageenan at 75° C., and/or a viscosity from about 30 to about 80 cP for an aqueous solution containing 1.5 wt. % the carrageenan at 75° C.). Such carrageenan-based compositions also can have any of the characteristics or properties provided below, and in any combination.

The carrageenan can comprise (or consist essentially of, or consist of) an iota carrageenan. The carrageenan also can comprise (or consist essentially of, or consist of) a kappa carrageenan. Thus, the compositions disclosed herein can contain an iota carrageenan; alternatively, a kappa carrageenan; or alternatively, a mixture or combination of an iota carrageenan and a kappa carrageenan.

Generally, the carrageenan has a relatively low potassium content, which is typically less than or equal to about 4 wt. %. While not wishing to be bound by the following theory, it is believed that carrageenans with higher potassium contents—such as in excess of 4 wt. %—result in compositions having fusion temperatures (and melt temperatures and gel temperatures; discussed further below) that are too high, and prevent the composition from being used as "drop in" replacement for gelatin-based capsule formulations. Thus, suitable potassium contents of the carrageenan can include, but are not limited to, less than or equal to about 3.5 wt. %, less than or equal to about 3 wt. %, less than or equal to about 2 wt. %, less than or equal to about 1.5 wt. %, less than or equal to about 1.3 wt. %, less than or equal to about 1 wt. %, or less than or equal to about 0.5 wt. %. Other appropriate ranges for the potassium content are readily apparent from this disclosure.

For instance, and not wishing to be bound by theory, it is also believed that a minimum level of potassium, such as 0.5 wt. %, can be beneficial for producing a consistent or uniform composition with the starch, plasticizer, and water (e.g., without lumps). Therefore, illustrative and non-limiting ranges for the potassium content of the carrageenan can include from about 0.5 to about 4 wt. %, from about 0.5 to about 3.5 wt. %, from about 0.5 to about 3 wt. %, from about 0.5 to about 2 wt. %, from about 0.5 to about 1.5 wt. %, from about 1 to about 1.5 wt. %, or from about 1.2 to about 1.3 wt. %.

The carrageenan typically contains low levels of both calcium and magnesium. While not being limited thereto, the calcium content of the carrageenan often can be less than or equal to about 3 wt. %, less than or equal to about 1.5 wt. %, less than or equal to about 0.7 wt. %, less than or equal to about 0.2 wt. %, less than or equal to about 0.05 wt. %, or less than or equal to about 0.02 wt. %. Likewise, the magnesium content of the carrageenan often can be less than or equal to about 2 wt. %, less than or equal to about 1 wt. %, less than or equal to about 0.7 wt. %, less than or equal to about 0.2 wt. %, less than or equal to about 0.08 wt. %, or less than or equal to about 0.03 wt. %. Other appropriate ranges for the calcium content and the magnesium content are readily apparent from this disclosure.

The viscosity of the carrageenan typically is selected such that the carrageenan-based composition can produce capsules on pressure-free rotary die equipment, which often processes gelatin-based formulations. While not wishing to be bound by theory, it is believed that high viscosity carrageenans (e.g., viscosities in excess of about 55-60 cP for a 0.1 M aqueous sodium chloride solution containing 1.5 wt. % of the carrageenan at 75° C., and/or viscosities in excess of about 85-100 cP for an aqueous solution containing 1.5 wt. % the carrageenan at 75° C.) result in formulations that do not function on the pressure-free rotary die equipment.

Generally, the viscosity of the carrageenan can fall within a range from about 10 to about 55 cP, from about 10 to about 50 cP, from about 12 to about 45 cP, from about 12 to about 40 cP, or from about 18 to about 33 cP. This viscosity is the viscosity of a 0.1 M aqueous sodium chloride solution containing 1.5 wt. % of the carrageenan at 75° C. However, while not wishing to be bound by the following theory, it is believed that if the viscosity of the carrageenan is too low, it can be difficult to form consistent or uniform compositions with the starch, plasticizer, and water (e.g., without lumps). Further, to compensate for the low viscosity (e.g., lower molecular weight), increased amounts of carrageenan may be required in order to form a composition suitable for pressure-free capsule formation. Therefore, in such circumstances, the viscosity of the carrageenan often falls within a range from about 20 to about 55 cP, from about 22 to about 50 cP, from about 25 to about 45 cP, from about 25 to about 40 cP, or from about 32 to about 33 cP. Other appropriate ranges for the viscosity of a 0.1 M aqueous sodium chloride solution containing 1.5 wt. % of the carrageenan at 75° C. are readily apparent from this disclosure.

Additionally or alternatively, the viscosity of the carrageenan can fall within a range from about 30 to about 80 cP, from about 35 to about 80 cP, from about 30 to about 75 cP, from about 35 to about 75 cP, from about 30 to about 60 cP, from about 35 to about 60 cP, from about 30 to about 50 cP, from about 35 to about 50 cP, or from about 39 to about 44 cP, and the like. This viscosity is the viscosity of an aqueous solution containing 1.5 wt. % of the carrageenan at 75° C. (without sodium chloride). Other appropriate ranges for the viscosity of an aqueous solution containing 1.5 wt. % of the carrageenan at 75° C. are readily apparent from this disclosure.

The carrageenan-based composition can contain any suitable amount of the carrageenan, such as from about 2.5 to about 10 wt. %, from about 4 to about 9 wt. %, from about 5 to about 9 wt. %, from about 4.5 to about 8.5 wt. %, from about 5 to about 8.5 wt. %, from about 5.5 to about 8.5 wt. %, from about 6.5 to about 7.5 wt. %, or from about 6.8 to about 7.1 wt. % carrageenan. These weight percentages are based on the total weight of the composition. Stated another way, the amount of carrageenan in the composition, on a dry basis, typically can range from about 8 to about 17 wt. %, from about 9 to about 16 wt. %, from about 10 to about 15 wt. %, from about 11 to about 14 wt. %, or from about 12 to about 14 wt. % carrageenan. These weight percentages are based on the total weight of the composition, excluding water. Other appropriate ranges for the amount of carrageenan in the composition are readily apparent from this disclosure.

Any suitable starch component can be used in the compositions disclosed herein, such that films, capsules, and other articles of manufacture can be formed from the composition. Illustrative and non-limiting examples of starch materials that can be used can include a potato starch, a pre-gelatinized modified corn starch, a pre-gelatinized acid thinned modified corn starch, an acid modified hydroxypropylated corn starch, a flash dried acid modified native corn dent starch, a hydroxypropylated acid modified tapioca starch, a modified corn starch, a modified high amylose corn starch, and the like, as well as any combination thereof.

The "starch" component encompasses, for instance, chemically modified starches such as hydroxypropylated starches, acid thinned starches, and the like. Various commercially-available starches can be used as the starch component in the disclosed compositions, and representative examples include, but are not limited to, PURE-COTE B760 and B790 (an acid-modified hydroxypropylated corn starch), PURE-COTE B793 (a pre-gelatinized modified corn starch), PURE-COTE B795 (a pre-gelatinized modified corn starch), and PURE-DENT B890 (modified corn starch), which are available from Grain Processing Corporation.

The carrageenan-based composition can contain any suitable amount of the starch, such as from about 10 to about 32 wt. %, from about 12 to about 32 wt. %, from about 14 to about 30 wt. %, from about 15 to about 28 wt. %, from about 17 to about 25 wt. %, or from about 21 to about 22 wt. % starch. These weight percentages are based on the total weight of the composition. Stated another way, the amount of starch in the composition, on a dry basis, typically can range from about 20 to about 55 wt. %, from about 25 to about 50 wt. %, from about 22 to about 46 wt. %, from about 28 to about 48 wt. %, from about 33 to about 43 wt. %, or from about 38 to about 41 wt. % starch. These weight percentages are based on the total weight of the composition, excluding water. Other appropriate ranges for the amount of starch in the composition are readily apparent from this disclosure.

While not a requirement, the amount of starch in the composition generally is greater than the amount of carrageenan in the composition. In such instances, the weight ratio of starch:carrageenan can fall within a range from about 1:1 to about 6:1, from about 1.5:1 to about 6:1, from about 1:1 to about 5:1, from about 1.5:1 to about 5:1, from about 2:1 to about 6:1, from about 2:1 to about 5:1, or from about 2.5:1 to about 3.5:1. Other appropriate ranges for the weight ratio of starch: carrageenan in the composition are readily apparent from this disclosure.

As with the starch component, any suitable plasticizer component can be used in the compositions disclosed herein, such that films, capsules, and other articles of manufacture can be formed from the composition. Illustrative and non-limiting examples of plasticizer materials that can be used can include glycerin, sorbitol, a propylene glycol, a polyethylene glycol, and the like, as well as any combination thereof. In particular aspects of this invention, the plasticizer can comprise glycerin and/or sorbitol, with the relative amounts of these materials selected based on the desired hardness or stiffness of the film, capsule, or other article of manufacture.

The carrageenan-based composition can contain any suitable amount of the plasticizer, such as from about 17 to about 37 wt. %, from about 18 to about 36 wt. %, from about 20 to about 35 wt. %, from about 20 to about 34 wt. %, from about 22 to about 32 wt. %, or from about 24 to about 28 wt. % plasticizer. These weight percentages are based on the total weight of the composition. Stated another way, the amount of plasticizer in the composition, on a dry basis, typically can range from about 30 to about 70 wt. %, from about 35 to about 65 wt. %, from about 40 to about 60 wt. %, from about 42 to about 58 wt. %, from about 45 to about 55 wt. %, or from about 46 to about 50 wt. % plasticizer. These weight percentages are based on the total weight of the composition, excluding water. Other appropriate ranges for the amount of plasticizer in the composition are readily apparent from this disclosure.

The amount of water in the "wet" carrageenan-based composition is not particularly limited, but generally can range from about 30 to about 60 wt. %, from about 35 to about 55 wt. %, from about 40 to about 55 wt. %, from about 35 wt. % to about 50 wt. %, from about 40 to about 50 wt. %, or from about 44 to about 46 wt. %.

These weight percentages are based on the total weight of the composition. As one of skill in the art would readily recognize, there is still water present in "dry" carrageenan-based compositions (e.g., films or capsules), and the amount of retained water often can be in the 2-14 wt. % range or 3-8 wt. % range. Other appropriate ranges for the amount of water in the compositions are readily apparent from this disclosure.

Compositions (or films, or capsules) in which component amounts are listed in weight percentages on a "dry basis" are intended to reflect the compositions as if no water is present. Such can be determined by drying and/or dehumidifying the composition (or film, or capsule) to remove the retained water.

If desired, the composition can further contain a buffer, a purpose of which can be to adjust or control the pH of the carrageenan-based composition and/or to improve the stability of any articles produced therefrom (e.g., films or capsules). Any suitable buffer can be used, such as a hydroxide, carbonate, citrate, or phosphate, or mixtures thereof and their salts (e.g., sodium or potassium). When present, the amount of the buffer in the carrageenan-based composition can be an amount greater than zero, but less than or equal to about 1 wt. %, less than or equal to about 0.5 wt. %, or less than or equal to about 0.3 wt. %. These weight percentages are based on the total weight of the composition. Other appropriate ranges for the amount of buffer in the composition are readily apparent from this disclosure.

Other ingredients or additives can be used in the carrageenan-based compositions, such as a colorant, a preservative, a disintegrant, a flavorant, and the like. Combinations of more than one of these other ingredients or additives can be used in the compositions disclosed herein.

While not being limited thereto, the carrageenan-based compositions typically can have a melt temperature ($T_M$) that falls within a range from about 30° C. to about 90° C., from about 55° C. to about 90° C., from about 30° C. to about 66° C., from about 55° C. to about 75° C., from about 60° C. to about 75° C., or from about 55° C. to about 70° C., and the like. Similarly, the gel temperature ($T_G$) of the composition is not particularly limited, but often falls in the range from about 20° C. to about 58° C., from about 30° C. to about 40° C., from about 32° C. to about 40° C., or from about 30° C. to about 38° C., and the like. Other appropriate ranges for the melt temperature ($T_M$) and gel temperature ($T_G$) are readily apparent from this disclosure.

The carrageenan-based compositions disclosed herein have a fusion temperature ($T_F$) or sealing temperature that makes them suitable for use (in making capsules) on pressure-free rotary die equipment and/or suitable to replace conventional gelatin-based capsule formulations. For instance, the fusion temperature ($T_F$) or sealing temperature of the carrageenan-based composition often can be in a range from about 25° C. to about 62° C., from about 25° C. to about 50° C., from about 30° C. to about 45° C., from about 35° C. to about 48° C., or from about 48° C. to about 60° C., and the like. Other appropriate ranges for the fusion temperature ($T_F$) are readily apparent from this disclosure.

Articles of Manufacture

Articles of manufacture can be formed from, and/or can comprise, the carrageenan-based compositions of this invention, whose typical properties, components, and characteristics are described herein.

The article of manufacture can be a film (e.g., a dry film). Thus, a film can be formed from, and/or can comprise, any of the carrageenan-based compositions described herein. The film can have any suitable average thickness, such as in a range from about 0.5 mm to about 3 mm, from about 0.7 to about 1.7 mm, or from about 0.75 to about 1.5 mm, while not being limited thereto. Further, the film can be configured to produce capsules on pressure-free rotary die equipment, as disclosed herein.

Also encompassed herein are capsules formed from and/or comprising any of the compositions disclosed herein. For example, a capsule contemplated herein can comprise a shell (e.g., a dry shell) comprising any of the disclosed carrageenan-based compositions, and a fill material. The shell encloses or encapsulates the fill material. The fill material is not particular limited. Thus, the fill material can be a liquid or a solid. The carrageenan-based capsules can be configured to replace gelatin-based capsules.

After formation of the carrageenan-based capsules, the capsules can be conventionally dried using heat. A tumble dryer can be used, and generally, wet capsules exiting the filling equipment/die can be conveyed directly to the tumble dryer. Typical tumble dryers can remove about 25 wt. % of the water present in the wet capsules, although not limited thereto. Once the capsules leave the tumble dryer, they can be spread onto (stackable) drying trays, then placed in a heated tunnel or drying room, in which air flows at a predetermined velocity with a known temperature and low humidity, thereby drying the capsules. Normally, the 2-stage drying process can last for 24 hours or more, depending on the water content in the capsules. Thus, the capsule drying process can significantly increase overall capsule manufacturing costs. Other options include dehumidifier and refrigeration techniques.

Consistent with aspects of this invention, the carrageenan-based capsule can be treated (or contacted) with an alcohol compound to remove at least a portion of the water from the capsule and/or to increase the rigidity (stiffness or hardness) of the capsule. Any suitable alcohol compound can be used, and the treatment or contacting can be performed for any suitable combination of time and temperature conditions. Beneficially, capsule rigidity can be increased significantly, and can be increased more than that achieved via conventional drying and cooling of capsules. Therefore, conventional drying using heat and subsequent cooling can be eliminated from the capsule production process.

The alcohol treatment process is described herein for capsules containing an iota carrageenan, which is characterized by a low potassium content and certain viscosity features. However, this alcohol treatment is not limited thereto, and is applicable to capsules containing any amount and any type of carrageenan, for instance, kappa carrageenans.

Various alcohol compounds can be used to treat the capsule, whether linear or branched, or a primary alcohol, a secondary alcohol, or a tertiary alcohol. Typically, the alcohol compound can comprise a hydrocarbyl alcohol, although this is not a requirement. For instance, the alcohol compound can comprise an alkyl alcohol, a cycloalkyl alcohol, an aryl alcohol, an arylalkyl alcohol, and the like, as well as combinations thereof.

The number of carbon atoms in the alcohol compound is not particularly limited, although in some aspects, the alcohol compound can comprise a $C_1$ to $C_{32}$ alcohol; alternatively, a $C_1$ to $C_{18}$ alcohol; alternatively, a $C_1$ to $C_{12}$ alcohol; alternatively, a $C_1$ to $C_8$ alcohol; alternatively, a $C_1$ to $C_4$ alcohol; alternatively, a $C_2$ to $C_{12}$ alcohol; or alternatively, a $C_2$ to $C_6$ alcohol. Representative and non-limiting examples of suitable alcohol compounds (e.g., mono-ol compounds) can include the following: methanol, ethanol, propanol (e.g., isopropanol, n-propanol), butanol (e.g., n-butanol, isobutanol), pentanol, hexanol, heptanol, octanol, decanol, hexadecanol, cyclohexanol, phenol, benzyl alcohol, and the like, as well as combinations thereof. In one aspect, the alcohol compound can comprise methanol, ethanol, propanol (e.g., isopropanol, n-propanol), butanol (e.g., n-butanol, isobutanol), pentanol, hexanol, heptanol, octanol, decanol, hexadecanol, and the like, or a combination thereof. In another aspect, the alcohol compound can comprise methanol, ethanol, isopropanol, n-propanol, and the like, or a combination thereof. In yet another aspect, the alcohol compound can comprise methanol; alternatively, ethanol; alternatively, isopropanol; or alternatively, n-propanol.

A concentrated alcohol often can be used, or an alcohol diluted in water. However, since water is desirably removed from the capsule, the addition of water typically is avoided during the contacting of the capsule and the alcohol compound. The alcohol treatment can be conducted at any suitable temperature, but often ranges from about 10° C. to about 40° C.; alternatively, from about 10° C. to about 30° C.; alternatively, from about 15° C. to about 30° C.; or alternatively, from about 20° C. to about 25° C. The duration of the alcohol treatment is not particularly limited, and can depend upon the water content of the capsule and the desired capsule rigidity. Illustrative treatment times range from about 15 min to about 96 hr, from about 30 min to about 72 hr, from about 30 min to about 48 hr, or from about 1 hr to about 24 hr, and so forth.

The treatment of the capsules with the alcohol compound can be conducted using any suitable technique and equipment. For instance, the capsules can be placed into a vessel or tank, and then filled with enough of the alcohol compound to exceed the level of the capsules in the vessel or tank. Optionally, agitation can be provided in the vessel or tank to increase the contact between the capsules and the alcohol compound. Alternatively, the capsules can be placed in a fixed or packed bed arrangement, and the alcohol compound can be contacted with the capsules by flowing the alcohol compound through the bed of the capsules. As would be recognized by those of skill in the art, other suitable techniques and equipment can be employed, and such techniques and equipment are encompassed herein.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The viscosity of the carrageenan was determined in a 0.1 M aqueous sodium chloride solution containing 1.5 wt. % of the carrageenan, based on the weight of all components in the solution, at 75° C. This viscosity was measured using a Brookfield LVF (Brookfield Engineering Laboratories, Inc.) viscometer using Spindle #1 at 60 rpm and determining the viscosity after six revolutions.

In addition, the viscosity of the carrageenan was determined for an aqueous solution containing 1.5 wt. % the carrageenan at 75° C. This viscosity was measured using a Brookfield LVF or LVT (Brookfield Engineering Laboratories, Inc.) viscometer using the appropriate spindle at 30 rpm and determining the viscosity after 30 seconds.

Potassium, calcium, and magnesium contents (in wt. %) of the carrageenan were determined by ICP-MS analysis of a sample digested in a mixture of nitric acid and hydrochloric acid.

The melt temperature ($T_M$) and gel temperature ($T_G$) of the carrageenan-based compositions can be determined as follows. The gelling temperature can be visually determined by watching the temperature in a melting tank as the composition is cooled. The gelling temperature is the temperature at which the composition no longer is flowing. The melting temperature was visually determined by taking a gelled sample of the composition, and heating it in a saucepan until it started to flow. The temperature at which the composition started to flow is the melting temperature.

The fusion temperature ($T_F$) of the carrageenan-based compositions was determined on a pressure-free rotary die machine operating at 2.8 rpm (of the die rolls) and a die roll pressure in the 0.1-0.4 kg/cm$^2$ range. The film thickness was in the 0.6-1.4 mm range. The fusion temperature ($T_F$) was determined by measuring the temperature in the wedge of the pressure-free rotary die machine. When a capsule could be made without leakage, that wedge temperature was defined as the fusion temperature.

Example 1A-3A

Carrageenan Materials

Properties of the iota carrageenan materials of Examples 1A-3A are summarized in Table I. Notably, the iota carrageenans spanned a wide range of viscosity (molecular weight) and potassium content.

The iota carrageenan of Example 1A was produced by an extraction procedure described in European Patent EP 1115748 B1, and after neutralization and fine filtration, was subjected to an ion exchange procedure described in U.S. Pat. No. 8,404,289. The iota carrageenan of Example 2A was traditionally extracted and then treated in accordance with U.S. Pat. No. 8,404,289. The iota carrageenan of Example 3A was produced in accordance with EP 1115748. These patent publications are incorporated herein by reference in their entirety.

Examples 1B-3B

Capsule Formulations and Production of Capsules

Samples of iota carrageenans 1A-3A were used to produce the respective carrageenan-based compositions of Examples 1B-3B, as summarized in Table II. The compositions were prepared by first adding the sodium hydrogen phosphate buffer salt to water. When the salt was fully dissolved, the solution was transferred to a tank, followed by addition of the starch component, and mixing for 10 min. Separately, the carrageenan and glycerin were mixed for 10 min (alternatively, the carrageenan can be dry blended with a portion of the starch, and the dry blend mixed with glycerin for 10 min). The resulting slurry was poured into the tank, followed by mixing at 90° C. for 1.5-2 hr. A vacuum was applied to the tank, while avoiding material overflow until bubbles were eliminated, followed by a de-aeration step. The tank temperature was maintained at 90° C. The resulting composition was fed to a rotary die machine equipped with pressure-free spreader box. The temperature of the wedge of the rotary die machine was adjusted to within the 25-62° C. range in order to determine useful fusion (sealing) temperatures for capsule production. The film thickness was in the 0.6-1.4 mm range.

Unexpectedly, Example 1B (using carrageenan 1A) performed the best, producing excellent soft capsules at fusion or sealing temperatures encompassing the 25-62° C. range. Excellent capsules were produced at fusion or sealing temperatures, for example, in the 32-45° C. range.

Example 2B (using carrageenan 2A) resulted in some lump formation during the combination of carrageenan and glycerin. However, these lumps were eliminated during the heating step to 90° C. in the melting tank. Pre-blending the carrageenan with some starch prior to addition to glycerin also eliminated lump formation. Unexpectedly, excellent capsules were made with fusion or sealing temperatures in the same range as for Example 1B.

Example 3B (using carrageenan 3A) could not be successfully converted into capsules. It is believed that the higher viscosity of carrageenan 3A resulted in inadequate distribution of the composition in the pressure-free spreader box. Further, and likely due to the higher potassium content of the carrageenan, capsule fusion/sealing could not be accomplished in the desired temperature range.

Examples 4B-6B

Capsule Formulations and Production of Capsules

Samples of iota carrageenan 1A were used to produce the carrageenan-based compositions of Examples 4B-6B, as summarized in Table III. The compositions were prepared by first adding the sodium hydrogen phosphate buffer salt to water. When the salt was fully dissolved, the solution was transferred to a tank, followed by addition of the starch component, and mixing for 10 min. Separately, the carrageenan and plasticizer were mixed for 10 min (alternatively, the carrageenan can be dry blended with a portion of the starch, and the dry blend mixed with plasticizer for 10 min). The resulting slurry was poured into the tank, followed by mixing at 90° C. for 1.5-2 hr. A vacuum was applied to the tank, while avoiding material overflow until bubbles were eliminated, followed by a de-aeration step. The tank temperature was maintained at 90° C. The resulting composition was fed to a rotary die machine equipped with pressure-free spreader box. The temperature of the wedge of the rotary die machine was adjusted to within the 48-60° C. range in order to determine useful fusion (sealing) temperatures for capsule production. The film thickness was in the 0.6-1.4 mm range.

Unexpectedly, Examples 4B-6B (using carrageenan 1A) produced excellent soft capsules at fusion or sealing temperatures encompassing the 48-60° C. range; the capsules had excellent physical properties and overall appearance. Temperatures below 48° C. were not tested, however, based on the performance at 48° C., it is believed that significantly lower fusion or sealing temperatures could have been used successfully, perhaps as low as 25-35° C.

Beneficially, excellent soft capsules were produced regardless of the relative amount of glycerin and sorbitol used as the plasticizer component of the carrageenan composition. It was surprisingly found that the relative amount of glycerin and sorbitol also impacted the capsule hardness or stiffness, with an increase in the relative amount of sorbitol (and a decrease in the relative amount of glycerin) resulting in an increase in capsule hardness or stiffness. Thus, the ratio of glycerin:sorbitol can be used to tailor capsule hardness or stiffness, as needed, for any particular end-use application.

Examples 7B-9B

Capsule Formulations and Production of Capsules

Samples of iota carrageenan 1A were used to produce the carrageenan-based compositions of Examples 7B-9B, as summarized in Table IV. The compositions were prepared by first adding the sodium hydrogen phosphate buffer salt to water. When the salt was fully dissolved, the solution was transferred to a tank, followed by addition of the starch component, and mixing for 10 min. Separately, the carrageenan and plasticizer were mixed for 10 min (alternatively, the carrageenan can be dry blended with a portion of the starch, and the dry blend mixed with plasticizer for 10 min). The resulting slurry was poured into the tank, followed by mixing at 90° C. for 1.5-2 hr. A vacuum was applied to the tank, while avoiding material overflow until bubbles were eliminated, followed by a de-aeration step. The tank temperature was maintained at 90° C. The resulting composition was fed to a rotary die machine equipped with pressure-free spreader box. The temperature of the wedge of the rotary die machine was adjusted to within the 48-60° C. range. Capsules having a length of 25 mm and a diameter of 8 mm were produced.

At room temperature (20-25° C.) and without drying, the resulting wet capsules (25 mm length, 8 mm diameter) were then treated in 100% isopropanol for varies time periods, after which the rigidity of the respective capsule was measured. The capsule was placed in a 100-mL Blue Cap flask and covered with 100% isopropanol for the desired time period, and after each treatment, the capsule was withdrawn from the flask, and wiped clean of alcohol. To measure rigidity, the capsule was placed on the bottom of a crystallizing dish (70 mm diameter, 40 mm height), and then deformed using the texture analyzer (TA·TX plus Texture Analyzer, 1 inch piston, 0.5 mm per second, 3 mm penetration). The piston covered the entire capsule. The capsule rigidity was measured as the force (in grams) required to deform the capsule by 1 mm, 2 mm, or 3 mm. After measuring the rigidity, the capsule was returned to the flask and covered with isopropanol for the next treatment time period.

Table V summarizes the rigidity of Example 7B capsules (glycerin) treated with isopropanol, Table VI summarizes the rigidity of Example 8B capsules (sorbitol) treated with isopropanol, and Table VII summarizes the rigidity of Example 9B capsules (2:1 glycerin:sorbitol) treated with isopropanol. At time zero, it is apparent that the relative amount of glycerin and sorbitol impacted the capsule hardness or stiffness (rigidity), with the capsules produced with all sorbitol (as the plasticizer) being the most rigid.

As shown in Table V and Table VII, for capsules containing all glycerin (as the plasticizer) or a mixture of glycerin and sorbitol (as the plasticizer), the rigidity of the capsule increased substantially by treating the wet capsules in isopropanol for a time period ranging from a few hours to a few days. Further, capsule rigidity increased with the isopropanol treatment time. As shown in Table VI, for capsules containing all sorbitol (as the plasticizer), the rigidity of the capsule also can be increased, but the treatment time should be short (e.g., 1 hour or less) to prevent capsule breakage. Table VIII summarizes the rigidity of Example 7B capsules (glycerin) treated with ethanol (96%), Table IX summarizes the rigidity of Example 7B capsules (glycerin) de-watered/dried at 40° C., Table X summarizes the rigidity of Example 9B capsules (2:1 glycerin:sorbitol) treated with ethanol, and Table XI summarizes the rigidity of Example 9B capsules (2:1 glycerin:sorbitol) de-watered/dried at 40° C. From these tables, ethanol treatment appears to as effective as isopropanol, but with ethanol a steady state for capsule rigidity was reached faster. For both alcohols, the rigidity generally was higher for alcohol treatment as compared to de-watering (drying) using heat at 40° C.

TABLE I

Carrageenan materials of Examples 1A-3A.

| Example | 1A | 2A | 3A |
|---|---|---|---|
| Viscosity (cP) - 1.5 wt. % in 0.1M NaCl | 32.5 | 18.3 | 57.3 |
| Viscosity (cP) - 1.5 wt. % in water | 44 | 39 | 130 |
| Potassium (wt. %) | 1.27 | 0.15 | 4.32 |
| Calcium (wt. %) | 0.01 | 0.004 | 0.09 |
| Magnesium (wt. %) | 0.02 | 0.003 | 0.16 |

TABLE II

Carrageenan-based compositions of Examples 1B-3B.

| Example | 1B | 2B | 3B |
|---|---|---|---|
| Carrageenan Example | 1A | 2A | 3A |
| Carrageenan (kg) | 3.4 | 3.4 | 3.4 |
| Water (kg) | 22.0 | 22.0 | 22.0 |
| Starch (kg)[1] | 10.6 | 10.6 | 10.6 |
| Na$_2$HPO$_4$ (kg) | 0.1 | 0.1 | 0.1 |
| Glycerin (kg) | 13.6 | 13.6 | 13.6 |
| $T_M$ (° C.) | <90 | <90 | >90 |
| $T_F$ (° C.) | 25-62 | 25-62 | N/A[2] |

Notes:
[1]The starch was PURE-COTE B790 from Grain Processing Corporation.
[2]Capsules could not be produced with Example 3B.

TABLE III

Carrageenan-based compositions of Examples 4B-6B.

| Example | 4B | 5B | 6B |
|---|---|---|---|
| Carrageenan Example | 1A | 1A | 1A |
| Carrageenan (kg) | 3.4 | 3.4 | 3.4 |
| Water (kg) | 22.0 | 22.0 | 22.0 |
| Starch (kg)[1] | 10.6 | 10.6 | 10.6 |
| Na$_2$HPO$_4$ (kg) | 0.1 | 0.1 | 0.1 |
| Glycerin (kg) | 8.0 | 4.0 | 0.0 |
| Sorbitol, 70% (kg) | 4.0 | 8.0 | 12.0 |
| $T_M$ (° C.) | <90 | <90 | >90 |
| $T_F$ (° C.) | 48-60 | 48-60 | 48-60 |

Note:
[1]The starch was PURE-COTE B790 from Grain Processing Corporation.

TABLE IV

Carrageenan-based compositions of Examples 7B-9B.

| Example | 7B | 8B | 9B |
|---|---|---|---|
| Carrageenan Example | 1A | 1A | 1A |
| Carrageenan (kg) | 3.4 | 3.4 | 3.4 |
| Water (kg) | 22.0 | 22.0 | 22.0 |
| Starch (kg)[1] | 10.6 | 10.6 | 10.6 |
| Na$_2$HPO$_4$ (kg) | 0.1 | 0.1 | 0.1 |
| Glycerin (kg) | 12.0 | 0.0 | 8.0 |
| Sorbitol, 70% (kg) | 0.0 | 12.0 | 4.0 |

Note:
[1]The starch was PURE-COTE B790 from Grain Processing Corporation.

TABLE V

Rigidity of Example 7B capsules (glycerin) treated with isopropanol.

| | Deformation force (g) | | |
|---|---|---|---|
| Time (hr) | 1 mm | 2 mm | 3 mm |
| 0 | 30 | 132 | 504 |
| 1 | 45 | 176 | 539 |
| 2 | 31 | 131 | 486 |
| 4 | 49 | 200 | 646 |
| 8 | 48 | 207 | 734 |
| 26 | 173 | 785 | 2148 |
| 74 | 362 | 1597 | 4068 |

TABLE VI

Rigidity of Example 8B capsules (sorbitol) treated with isopropanol.

| | Deformation force (g) | | |
|---|---|---|---|
| Time (hr) | 1 mm | 2 mm | 3 mm |
| 0 | 399 | 1482 | 3963 |
| 1 | 752 | 2539 | 5209 |
| 2 | 802 | 2564 | 3173 |

TABLE VII

Rigidity of Example 9B capsules (2:1 glycerin:sorbitol) treated with isopropanol.

| | Deformation force (g) | | |
|---|---|---|---|
| Time (hr) | 1 mm | 2 mm | 3 mm |
| 0 | 24 | 109 | 408 |
| 1 | 39 | 157 | 498 |
| 2 | 31 | 133 | 496 |
| 4 | 48 | 195 | 628 |
| 8 | 50 | 220 | 767 |
| 26 | 133 | 589 | 1698 |
| 74 | 308 | 1371 | 3558 |

TABLE VIII

Rigidity of Example 7B capsules (glycerin) treated with ethanol.

| | Deformation force (g) | | |
|---|---|---|---|
| Time (hr) | 1 mm | 2 mm | 3 mm |
| 24 | 334 | 1237 | 2585 |
| 48 | 284 | 1213 | 2715 |

TABLE IX

Rigidity of Example 7B capsules (glycerin) de-watered at 40° C.

| Time (hr) | Deformation force (g) | | |
|---|---|---|---|
| | 1 mm | 2 mm | 3 mm |
| 24 | 116 | 530 | 1832 |
| 48 | 185 | 822 | 2627 |

TABLE X

Rigidity of Example 9B capsules (2:1 glycerin:sorbitol) treated with ethanol.

| Time (hr) | Deformation force (g) | | |
|---|---|---|---|
| | 1 mm | 2 mm | 3 mm |
| 24 | 305 | 1175 | 2498 |
| 48 | 316 | 1307 | Break |

TABLE XI

Rigidity of Example 9B capsules (2:1 glycerin:sorbitol) de-watered at 40° C.

| Time (hr) | Deformation force (g) | | |
|---|---|---|---|
| | 1 mm | 2 mm | 3 mm |
| 24 | 159 | 693 | 2219 |
| 48 | 248 | 1064 | 3154 |

The invention is described above with reference to numerous aspects, embodiments, and specific examples. Many variations will suggest themselves to those skilled in the art in light of the above detailed description. All such obvious variations are within the full intended scope of the appended claims. Other aspects, embodiments, and/or features of the invention can include, but are not limited to, the following (which are described as "comprising" but, alternatively, can "consist essentially of" or "consist of"):

(1) A composition comprising a carrageenan, a starch, a plasticizer, and water, wherein the carrageenan has a potassium content of less than or equal to about 4 wt. % and is characterized by (i) a viscosity of from about 10 to about 55 cP for a 0.1 M aqueous sodium chloride solution containing 1.5 wt. % of the carrageenan at 75° C., and/or by (ii) a viscosity of from about 30 to about 80 cP for an aqueous solution containing 1.5 wt. % of the carrageenan at 75° C.

(2) The composition defined in (1), wherein the potassium content of the carrageenan is in any suitable range, or in any range disclosed herein, e.g., less than or equal to about 3 wt. %, less than or equal to about 1.3 wt. %, from about 0.5 to about 3 wt. %, or from about 0.5 to about 2 wt. %.

(3) The composition defined in (1) or (2), wherein the viscosity of the 0.1 M aqueous sodium chloride solution containing 1.5 wt. % of the carrageenan at 75° C. is in any suitable range, or in any range disclosed herein, e.g., from about 10 to about 50 cP, from about 12 to about 45 cP, from about 25 to about 45 cP, or from about 18 to about 33 cP; and/or the viscosity of the aqueous solution containing 1.5 wt. % the carrageenan at 75° C. (without sodium chloride) is in any suitable range, or in any range disclosed herein, e.g., from about 30 to about 80 cP, from about 35 to about 80 cP, from about 35 to about 60, from about 35 to about 50 cP, or from about 39 to about 44 cP.

(4) The composition defined in any one of (1)-(3), wherein the carrageenan comprises an iota carrageenan.

(5) The composition defined in any one of (1)-(4), wherein the carrageenan comprises a kappa carrageenan.

(6) The composition defined in any one of (1)-(5), wherein the carrageenan contains any suitable amount of calcium, or an amount in any range disclosed herein, e.g., less than or equal to about 3 wt. %, less than or equal to about 1.5 wt. %, less than or equal to about 0.7 wt. %, or less than or equal to about 0.02 wt. %.

(7) The composition defined in any one of (1)-(6), wherein the carrageenan contains any suitable amount of magnesium, or an amount in any range disclosed herein, e.g., less than or equal to about 2 wt. %, less than or equal to about 1 wt. %, less than or equal to about 0.7 wt. %, or less than or equal to about 0.03 wt. %.

(8) The composition defined in any one of (1)-(7), wherein the starch comprises any suitable starch, or any starch disclosed herein, e.g., a potato starch, a pre-gelatinized modified corn starch, a pre-gelatinized acid thinned modified corn starch, an acid modified hydroxypropylated corn starch, a flash dried acid modified native corn dent starch, a hydroxypropylated acid modified tapioca starch, a modified corn starch, a modified high amylose corn starch, or any combination thereof.

(9) The composition defined in any one of (1)-(8), wherein the plasticizer comprises any suitable plasticizer, or any plasticizer disclosed herein, e.g., glycerin, sorbitol, a propylene glycol, a polyethylene glycol, or any combination thereof

(10) The composition defined in any one of (1)-(9), wherein the composition contains an amount of water in any suitable range, or in any range disclosed herein, e.g., from about 30 to about 60 wt. %, from about 35 to about 55 wt. %, from about 40 to about 50 wt. %, or from about 44 to about 46 wt. %.

(11) The composition defined in any one of (1)-(10), wherein the composition further comprises a buffer.

(12) The composition defined in (11), wherein the composition contains any suitable amount of buffer, or an amount in any range disclosed herein, e.g., less than or equal to about 1 wt. %, less than or equal to about 0.5 wt. %, or less than or equal to about 0.3 wt. %.

(13) The composition defined in any one of (1)-(12), wherein the weight ratio of starch:carrageenan is any suitable weight ratio, or a weight ratio in any range disclosed herein, e.g., from about 1:1 to about 6:1, from about 1:1 to about 5:1, from about 1.5:1 to about 5:1, or from about 2:1 to about 5:1.

(14) The composition defined in any one of (1)-(13), wherein the composition contains an amount of carrageenan in any suitable range, or in any range disclosed herein, e.g., from about 2.5 to about 10 wt. %, from about 4 to about 9 wt. %, from about 5 to about 9 wt. %, from about 5.5 to about 8.5 wt. %, or from about 6.8 to about 7.1 wt. %.

(15) The composition defined in any one of (1)-(14), wherein the composition contains an amount of carrageenan in any suitable range, or in any range disclosed herein, e.g., from about 8 to about 17 wt. %, from about 10 to about 15 wt. %, from about 11 to about 14 wt. %, or from about 12 to about 14 wt. %, on a dry basis.

(16) The composition defined in any one of (1)-(15), wherein the composition contains an amount of plasticizer in any suitable range, or in any range disclosed herein, e.g., from about 17 to about 37 wt. %, from about 20 to about 35 wt. %, from about 22 to about 32 wt. %, or from about 24 to about 28 wt. %.

(17) The composition defined in any one of (1)-(16), wherein the composition contains an amount of plasticizer in any suitable range, or in any range disclosed herein, e.g., from about 30 to about 70 wt. %, from about 40 to about 60 wt. %, from about 45 to about 55 wt. %, or from about 46 to about 50 wt. %, on a dry basis.

(18) The composition defined in any one of (1)-(17), wherein the composition contains an amount of starch in any suitable range, or in any range disclosed herein, e.g., from about 10 to about 32 wt. %, from about 14 to about 30 wt. %, from about 17 to about 25 wt. %, or from about 21 to about 22 wt. %.

(19) The composition defined in any one of (1)-(18), wherein the composition contains an amount of starch in any suitable range, or in any range disclosed herein, e.g., from about 20 to about 55 wt. %, from about 25 to about 50 wt. %, from about 33 to about 43 wt. %, or from about 38 to about 41 wt. %, on a dry basis.

(20) The composition defined in any one of (1)-(19), wherein the composition further comprises any suitable additive, or any additive disclosed herein, e.g., a colorant, a preservative, a disintegrant, a flavorant, or any combination thereof.

(21) The composition defined in any one of (1)-(20), wherein the composition has a melt temperature ($T_M$) in any suitable range, or in any range disclosed herein, e.g., from about 30° C. to about 90° C., from about 55° C. to about 90° C., from about 60° C. to about 75° C., or from about 55° C. to about 70° C.

(22) The composition defined in any one of (1)-(21), wherein the composition has a fusion temperature ($T_F$) in any suitable range, or in any range disclosed herein, e.g., from about 25° C. to about 62° C., from about 25° C. to about 50° C., from about 30° C. to about 45° C., or from about 35° C. to about 48° C.

(23) The composition defined in any one of (1)-(22), wherein the composition has a gel temperature ($T_G$) in any suitable range, or in any range disclosed herein, e.g., from about 20° C. to about 58° C., from about 30° C. to about 40° C., from about 32° C. to about 40° C., or from about 30° C. to about 38° C.

(24) An article of manufacture comprising (or formed from) the composition defined in any one of (1)-(23).

(25) A film comprising (or formed from) the composition defined in any one of (1)-(23).

(26) The film defined in (25), wherein the film has any suitable average thickness, or an average thickness in any range disclosed herein, e.g., from about 0.5 mm to about 3 mm, or from about 0.75 to about 1.5 mm.

(27) The film defined in (25) or (26), wherein the film (or composition) is configured to produce capsules on pressure-free rotary die equipment.

(28) A capsule comprising: a shell comprising (or formed from) the composition defined in any one of (1)-(23), and a fill material.

(29) The capsule defined in (28), wherein the fill material is a liquid.

(30) The capsule defined in (28), wherein the fill material is a solid.

(31) The capsule defined in any one of (28)-(30), wherein the capsule is configured to replace a gelatin-based capsule.

(32) A method for removing water from a capsule and/or for increasing rigidity of a capsule, the method comprising contacting the capsule defined in any one of (28)-(31) with an alcohol compound.

(33) The method defined in (32), wherein the alcohol compound comprises methanol, ethanol, n-propanol, isopropanol, or any combination thereof

We claim:

1. A composition comprising:
    a carrageenan having a potassium content of less than or equal to about 4 wt. % and characterized by:
        (i) a viscosity of a 0.1 M aqueous sodium chloride solution containing 1.5 wt. % of the carrageenan in a range from about 25 to about 45 cP at 75° C., and/or
        (ii) a viscosity of an aqueous solution containing 1.5 wt. % of the carrageenan in a range from about 35 to about 60 cP at 75° C.;
    a starch;
    a plasticizer; and
    water;
    wherein the carrageenan comprises an iota carrageenan.

2. The composition of claim 1, wherein the carrageenan contains:
    from about 0.5 to about 2 wt. % potassium;
    less than or equal to about 3 wt. % calcium; and
    less than or equal to about 2 wt. % magnesium.

3. The composition of claim 1, wherein:
    the starch comprises a potato starch, a pre-gelatinized modified corn starch, a pre-gelatinized acid thinned modified corn starch, an acid modified hydroxypropylated corn starch, a flash dried acid modified native corn dent starch, a hydroxypropylated acid modified tapioca starch, a modified corn starch, a modified high amylose corn starch, or any combination thereof; and
    the plasticizer comprises glycerin, sorbitol, a propylene glycol, a polyethylene glycol, or any combination thereof.

4. The composition of claim 1, wherein the plasticizer comprises glycerin and/or sorbitol.

5. The composition of claim 1, wherein the composition contains from about 30 to about 60 wt. % water.

6. The composition of claim 1, wherein the composition further comprises from greater than zero to less than or equal to about 1 wt. % of a buffer.

7. The composition of claim 1, wherein a weight ratio of starch:carrageenan is in a range from about 1.5:1 to about 5:1.

8. The composition of claim 1, wherein the composition contains from about 4 to about 9 wt. % carrageenan.

9. The composition of claim 1, wherein the composition contains from about 17 to about 37 wt. % plasticizer.

10. The composition of claim 1, wherein the composition contains from about 10 to about 32 wt. % starch.

11. The composition of claim 1, wherein the composition further comprises an additive selected from a colorant, a preservative, a disintegrant, a flavorant, or any combination thereof.

12. The composition of claim 1, wherein the composition has a fusion temperature ($T_F$) in a range from about 25° C. to about 62° C.

13. The composition of claim 1, wherein the composition is configured to produce capsules on pressure-free rotary die equipment.

14. An article of manufacture comprising the composition of claim 1.

15. A film comprising the composition of claim 1.

16. The film of claim 15, wherein the film has an average thickness in a range from about 0.5 mm to about 3 mm.

17. The film of claim 15, wherein the film contains, on a dry basis:

from about 10 to about 15 wt. % carrageenan;
from about 40 to about 60 wt. % plasticizer; and
from about 25 to about 50 wt. % starch.

18. A capsule comprising:
a shell comprising the composition of claim 1; and
a fill material.

19. The capsule of claim 18, wherein:
the shell contains, on a dry basis:
from about 10 to about 15 wt. % carrageenan;
from about 40 to about 60 wt. % plasticizer; and
from about 25 to about 50 wt. % starch; and
the fill material is a liquid or a solid.

20. A method for removing water from a capsule and/or for increasing rigidity of a capsule, the method comprising contacting the capsule of claim 18 with an alcohol compound.

21. A composition comprising:
a carrageenan having a potassium content of less than or equal to about 3 wt. % and a calcium content of less than or equal to about 0.7 wt. %, and characterized by:
(i) a viscosity of a 0.1 M aqueous sodium chloride solution containing 1.5 wt. % of the carrageenan in a range from about 10 to about 55 cP at 75° C., and/or
(ii) a viscosity of an aqueous solution containing 1.5 wt. % of the carrageenan in a range from about 30 to about 80 cP at 75° C.;
a starch;
a plasticizer; and
water;
wherein the carrageenan comprises an iota carrageenan.

22. The composition of claim 21, wherein:
the composition contains:
from about 4 to about 9 wt. % carrageenan;
from about 17 to about 37 wt. % plasticizer; and
from about 10 to about 32 wt. % starch; and
the carrageenan contains:
less than or equal to about 2 wt. % potassium;
less than or equal to about 0.2 wt. % calcium; and
less than or equal to about 0.2 wt. % magnesium.

23. The composition of claim 22, wherein the composition further comprises:
from greater than zero to less than or equal to about 1 wt. % of a buffer; and
an additive selected from a colorant, a preservative, a disintegrant, a flavorant, or any combination thereof.

24. A film comprising the composition of claim 21, wherein the film contains, on a dry basis:
from about 10 to about 15 wt. % carrageenan;
from about 40 to about 60 wt. % plasticizer; and
from about 25 to about 50 wt. % starch.

25. A capsule comprising:
a shell comprising the composition of claim 21, wherein the shell contains, on a dry basis:
from about 10 to about 15 wt. % carrageenan;
from about 40 to about 60 wt. % plasticizer; and
from about 25 to about 50 wt. % starch; and
a fill material.

26. A method for removing water from a capsule and/or for increasing rigidity of a capsule, the method comprising contacting the capsule of claim 25 with an alcohol compound.

* * * * *